United States Patent [19]

Lemchen et al.

[11] 4,192,070
[45] Mar. 11, 1980

[54] ORTHODONTIC DEVICES

[76] Inventors: Marc S. Lemchen, 219 E. 81st St., New York, N.Y. 10028; Ian M. Chong, 17 Monroe Pl. #1A, Brooklyn Heights, N.Y. 11201; Carlton Klein, 69-05C 186 La., Fresh Meadows, N.Y. 11365

[21] Appl. No.: 869,420
[22] Filed: Jan. 16, 1978
[51] Int. Cl.² ............................................. A61C 7/00
[52] U.S. Cl. ....................................................... 433/11
[58] Field of Search ........................................ 32/14 A

[56] References Cited

U.S. PATENT DOCUMENTS

| | | | |
|---|---|---|---|
| 1,166,766 | 4/1916 | Kelsey | 32/14 A |
| 3,076,265 | 2/1963 | Moore | 32/14 A |

Primary Examiner—Robert Peshock
Attorney, Agent, or Firm—Jordan and Hamburg

[57] ABSTRACT

An orthodontic device comprises means defining a passage for an arch wire and means defining a tension spring for bearing against the arch wire. The tension spring has a free end portion for bearing against the arch wire and is fixed at its other end relative to the rest of the device. The tension spring locks against the arch wire to prevent relative movement of the arch wire to the device toward the other end of the spring and yields to the arch wire to permit relative movement of the arch wire to the device toward the free end of the spring. The device may be used in combination with a conventional buccal tube or orthodontic bracket, being located mesially or distally thereof or integrated with the buccal tube or orthodontic bracket. The device may further comprise a member having a channel defined through it. The channel is of larger cross section than the cross section of the arch wire to permit free movement of the arch wire in the channel. The member is of smaller cross section than the passage in the device to permit insertion of the member into the device. The spring bears against the member instead of against the arch wire when the member is inserted in the device.

8 Claims, 16 Drawing Figures ical devices.

ORTHODONTIC DEVICES

BACKGROUND OF THE INVENTION AND PRIOR ART STATEMENT

This invention relates to orthodontic devices.

Orthodontics is, unfortunately, to a significant degree characterized by unintentional inflicting of discomfort upon the patient. The bending and cinching of arch wires result in projections which frequently act as irritants. For example, regarding the conventional buccal tubes which are used to anchor the ends of arch wires, a free end of an arch wire after being inserted through a buccal tube is locked relative to the buccal tube by cinching or bending. Buccal tubes are mounted on molars and orthodontic brackets are mounted on molars or other teeth by means of orthodontic bands or adhesive bonding. An orthodontic bracket serves to guide and position an arch wire relative to the tooth in which the orthodontic bracket is mounted and to help transmit forces from the arch wire to that tooth. Most orthodontic brackets do not lock relative to the arch wire, which frequently makes it necessary for the orthodontist to bend the arch wire for locking purposes in addition to whatever bends may be made in the arch wire solely for the purposes of selectively applying linear forces and torques to the patient's teeth. This amounts to additional work for the orthodontist and the creation of additional potential irritants in the mouth of the patient. On the other hand, prior art lockable orthodontic brackets are difficult to manipulate. The following U.S. patents are of some interest with respect to the present invention but the various devices thereof are all clearly distinguishable from the present invention and the present invention is entirely unobvious in view of such prior art.

The buccal tubes of FIG. 24 of U.S. Pat. No. 3,964,165 are free of the disadvantage of conventional buccal tubes in which the wire is guided through the tube and the free end, which projects through the tube, can be an irritant in the patient's mouth. This buccal tube, however, is constructed very much differently from the devices of the present invention and, moreover, unlike the devices of the present invention is not disclosed for use also in conjunction with an orthodontic bracket.

U.S. Pat. No. 3,838,514 relates to a conventional buccal tube or bracket. It appears that when this device is used as a buccal tube, it may not be necessary to extend the wire so far that it projects out of the buccal tube. The construction of this device is, however, very much different from the devices of the present invention.

U.S. Pat. No. 3,724,074 relates to orthodontic brackets having wire clamping capability. The clamping mechanism, however, is entirely different from the present invention.

U.S. Pat. No. 3,494,034 relates to a buccal tube insert for converting a buccal tube for use with arch wires of different cross sections. This patent is of interest only in connection with a feature of the present invention in which there is provided a slip tube for insertion in a device of the invention to permit the device to float freely on an arch wire. However, the inserts of the aforementioned patent are, in principle, entirely distinct from a slip tube of the present invention.

U.S. Pat. No. 3,486,231 is simply of general interest in that it discloses a different kind of buccal tube. This buccal tube has a clamping feature which is distinctly mechanically different from the manner of locking of a device of the present invention. In the aforementioned patent, the locking member is a wedge or a threaded element adapted to be received in the body of the buccal tube to bear against the arch wire end.

The orthodontic spring clip fastening system of U.S. Pat. No. 3,458,031, like the device of the present invention, eliminates undesirable wire pigtails. However, in construction, it is quite distinct from a device of the present invention.

U.S. Pat. No. 3,210,818 also discloses an arch wire clamping device. There is, however, no essential structural similarity to a device of the present invention.

In U.S. Pat. No. 415,829, an end portion of the arch wire has a rack formed thereon which cooperates with a dog attached to the buccal tube to permit adjustment of the tension of the arch wire. A device of the present invention, however, is not a rack and dog arrangement and permits infinite adjustment rather than mere stepwise adjustment, as well as free floating of the wire if desired.

It is an object of the invention to provide novel orthodontic devices to be used with an "edgewise" or "light wire" technique and which eliminate the disadvantages characteristic of the prior art. "Edgewise" or "light wire" orthodontic techniques per se, in which arch wires are utilized, are well known.

It is a further, more specific object of the invention to provide novel orthodontic devices which are releasably lockable relative to arch wires and which move in one direction relative to the arch wire and lock in the other direction.

Other objects and advantages of the present invention will be apparent from the following description thereof.

SUMMARY OF THE INVENTION

The present invention provides orthodontic devices for use with an edgewise or light wire orthodontic device. A device of the invention can be used on any or all individual teeth, being mounted on teeth, like other orthodontic devices, by conventional means, namely orthodontic bands or adhesive bonding. A device of the invention can be placed on the distal end of an arch wire after the wire is passed through a conventional orthodontic tube. Apart from being used with an orthodontic tube, such as a buccal tube, a device of the invention can be integrated with a conventional orthodontic tube. A device of the invention can be integrated with a conventional orthodontic bracket or used in place of a conventional orthodontic bracket or it can be attached mesially or distally to the bracket.

Devices of the invention are releasably lockable relative to arch wires. The device permits relative movement of the arch wire and the device in one direction only. This makes bending or cinching of the arch wire ends unnecessary. Also, the device may serve as a novel stop for tying segments of teeth together or preventing undesirable individual tooth or segment movement. Simple use of a conventional dental tool, such as a probe, unlocks the device. An additional device, which may conveniently be referred to as "slip tube," is provided according to the invention to hold open the lockable device of the invention so that the lockable device and arch wire can slide relative to each other freely in both directions.

Structurally, an orthodontic device according to the invention comprises means defining a passage for an arch wire and means defining a tension spring for bearing against the arch wire. The tension spring has a free end portion for bearing against the arch wire and is fixed at its other end relative to the rest of the device. The tension spring locks against the arch wire to prevent relative movement of the arch wire and the device toward the other end of the spring and yields to the arch wire to permit relative movement of the arch wire and the device toward the free end of the spring. The device may be used in combination with a conventional buccal tube or orthodontic bracket, being located mesially or distally thereof or integrated with the buccal tube or orthodontic bracket. The aforementioned additional device or "slip tube" may comprise a member having a channel defined through it. The channel is of larger cross section than the cross section of the arch wire to permit free movement of the arch wire in the channel. The member is of smaller cross section than the passage in the locking device to permit insertion of the member into the locking device. The spring bears against the member instead of against the arch wire when the member is inserted in the locking device.

Use of the devices of the invention makes unnecessary cinching back or tying back arches. Arches can be activated by pushing them through locking devices of the invention and released for removal without distortion or mutilation. The discomfort caused by the cinching process is avoided. No wire has to extend out of the posterior part of a buccal tube, eliminating a major source of patient discomfort.

Use of the devices of the invention permits the use of arches of very high grade alloy wires which would not generally be used if multilation occurred upon removal or activation of the arch. The devices of the invention are also ideally suited for non-metallic wires which would otherwise require exotic techniques for cinching or activation within the oral cavity.

A further application of devices of the invention is the use thereof on teeth other than the tooth most posterior on the appliance in order to utilize functional force orthodontic tooth movement. Teeth rock during chewing and this may be referred to as movement of the teeth due to the application thereto of functional forces. Normally the net effect of this movement on the relative positions of the teeth is essentially zero. It can readily be appreciated, however, that since a locking device of the invention permits relative motion of the arch wire and the locking device only in one direction, if a tooth to which such a locking device is attached happens to rock in the direction in which the device will move on the wire, the device will prevent the tooth from returning to its original position and, very slowly, by repeated such occurrences the tooth will be shifted to a desired new position.

DESCRIPTION OF PREFERRED EMBODIMENTS

Figure 1:
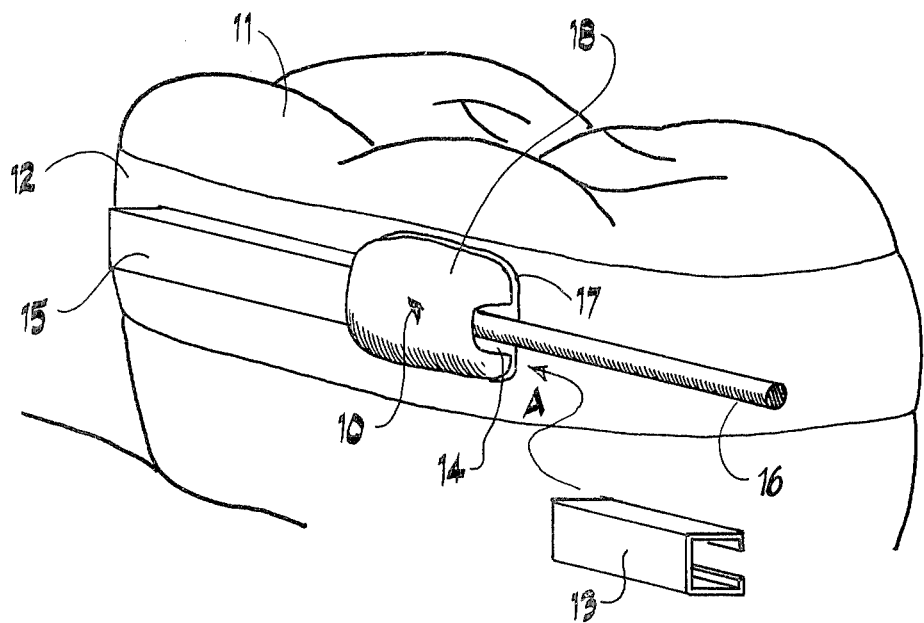
FIG. 1 is an isometric view of an orthodontic device according to the invention mounted on a tooth by means of an orthodontic band, receiving an arch wire and including a supplemental part therefor.

In FIG. 1, a locking device 10 according to the invention is shown mounted on a molar 11 by means of an orthodontic band 12 to which the device 10 is welded. A channel-shaped member 13 which, with regard to its function, may conveniently be referred to as "slip tube," is insertable in passage 14 of the device 10, as shown by arrow A. Welded to the orthodontic band 12 is also a conventional buccal tube 15, the device 10 being located mesially of the tube 15. An arch wire 16 is received in the passage 14 of the device 10. The end of the wire 16 is received in the buccal tube 15. The device 10 locks the wire 16 to prevent only mesial movement of the wire 16 relative to the device 10, the wire 16 being free to move distally relative to the device 10. Because of the locking effected by the device 10, the wire 16 is not projected through the distal end of the device 10 since conventional cinching has been made unnecessary by the device 10.

Figure 2:
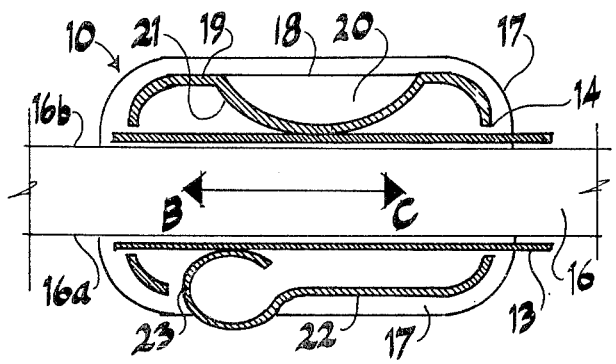
FIG. 2 is a cross section of the device according to FIG. 1 including the supplemental part inserted therein.
Figure 3:
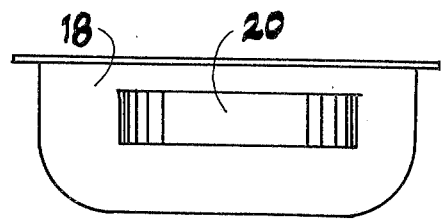
FIG. 3 is a top view of the aforementioned device.
Figure 5:
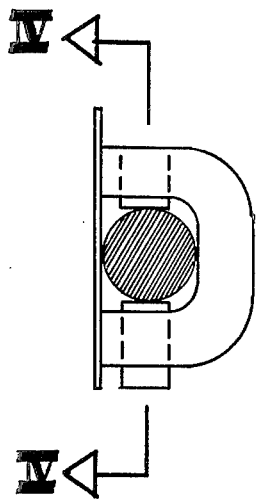
FIG. 5 is an end view of the aforementioned device.
Figure 4:
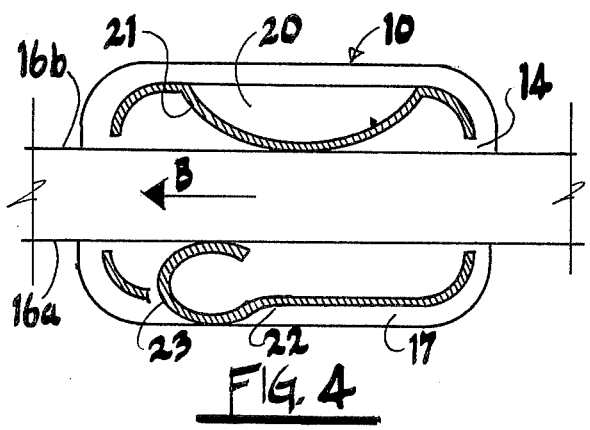
FIG. 4 is a cross section of the aforementioned device.

As shown in FIGS. 1-5 and 7, the device 10 includes a base plate 17 having a shell 18 welded thereon. A passage 14 is formed through the shell 18. One wall 19 of the shell 18 has formed therein an indentation 20 defining an anvil 21. The opposite wall 22 of the shell 18 is formed in part into a tension spring 23. In FIG. 2, the slip tube 13 is illustrated inserted into the passage 14. Suppose, however, that the slip tube was not inserted, which is shown in FIG. 4. The spring 23 would bear against adjacent edge 16a of the wire 16, urging the opposite edge 16b of the wire 16 against the anvil 21. It can readily be appreciated, in accordance with well understood mechanical principles, that, when the wire 16 is urged in the direction of arrow B, the spring 23 will immediately yield downwardly to permit motion of the wire 16 in the direction of arrow B in FIGS. 2 and 4, and when the wire 16 is urged in the opposite direction, the spring 23 will immediately pull upwardly, whereby the wire 16 is locked between the spring 23 and the anvil 21, preventing motion of the wire 16 in the direction of arrow C in FIG. 2. It will readily be appreciated that, analogously, the spring 23 will permit the slip tube 13 to be inserted fully into the passage 14 of the device 10 from one end of the passage 14 but not from the opposite end of the passage 14. (Throughout the application, the convention is followed of labeling an arrow pointing in the direction in which the device according to the invention will move relative to the arch wire, except in FIGS. 4 and 6.)

Figure 6:
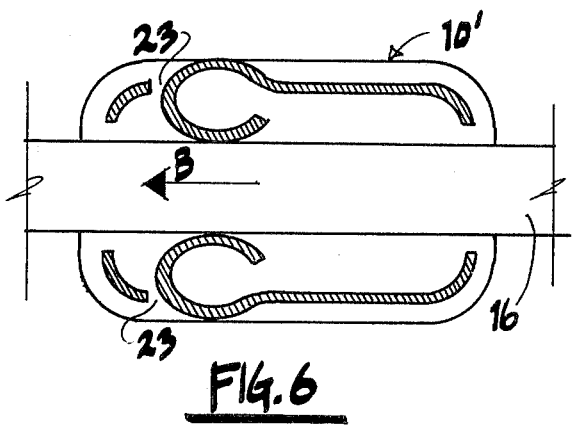
FIG. 6 is a cross section analogous to FIG. 4 of a modification of the device of FIGS. 1-5.
Figure 7:
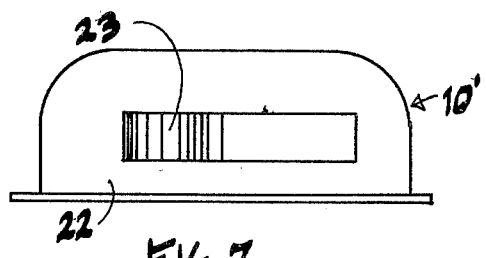
FIG. 7 is a bottom view of the device of FIG. 6.

A modified locking device 10' according to the invention is illustrated in FIG. 6, which device 10' is in all respects but for one like that of the device 10. Namely, the device 10' is provided with two tension springs 23, one of which takes the place of the anvil 21. Functionally, the device 10' is exactly like the device 10, the two springs 23 in the device 10' responding exactly like the single signal 23 in the device 10, namely the wire 16 can move in the device 10' only in the direction indicated by arrow B in FIG. 6.

It will be apparent to orthodontists that the devices according to the invention have many applications. In that regard it is to be remembered that the devices of the invention may be inverted so that they will permit motion of the wire relative to the device in either direction. FIGS. 8–16 are merely exemplary of the very numerous applications in which the present invention may be used.

Figure 8:
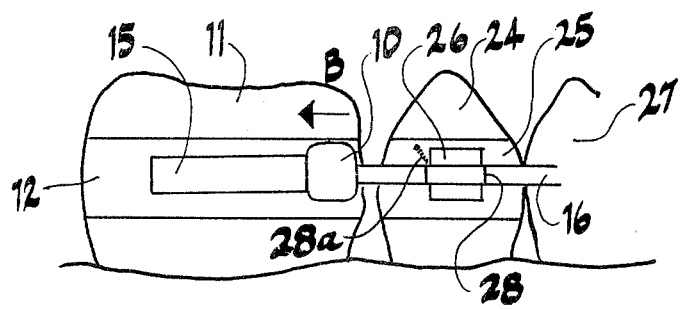
FIG. 8 is an elevation view including a device according to the invention mounted on a tooth by means of an orthodontic band and receiving an arch wire or mounted on wire unattached to tooth.

In FIG. 8, the conventional buccal tube 15 is mounted on the molar 11 by means of the conventional orthodontic band 12. The arrangement of the devices on the molar 11 is exactly like that illustrated in FIG. 1 except that the slip tube 13 is not inserted, nor is the device welded or attached to the orthodontic band 12 in any manner. Mounted on the adjacent premolar 24 by means of a conventional orthodontic band 25 is a conventional orthodontic bracket 26. Arch wire 16 is engaged by the orthodontic bracket 26 (the tie wire 28, which is twisted at 28a, fastening the wire 16 to the bracket 26 in the conventional manner), the device 10 and, finally, the buccal tube 15. One or more teeth 27, (only one of which is illustrated) adjacent to the tooth 24 in the mesial direction may also be provided with orthodontic bands and brackets (not illustrated). The device 10 herein is acting as a "stop" to prevent distal movement of the arch wire. The device 10 is capable of sliding in the direction of arrow B thus preventing the arch wire 16 from moving in that same direction. This action enables the molars 11 to be used as "anchor" teeth and/or to enable the molar 11 to be driven distally using the anterior teeth 27 and premolars 24 as anchors as a complete unit. The device 10 may or may not be welded or attached to the orthodontic band 12.

Figure 9:
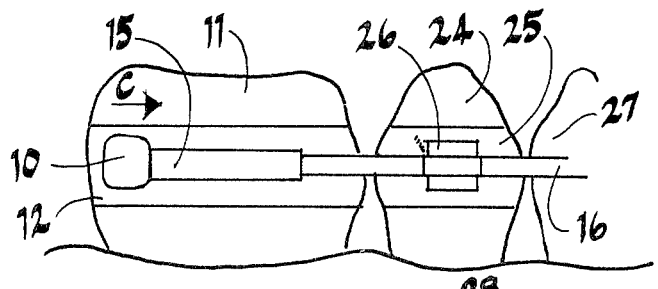
FIG. 9 is an elevation view including a device according to the invention mounted on an arch wire, the device being attached or unattached to the orthodontic band.

The arrangement of FIG. 9 is similar to that of FIG. 8 except that the device 10 is located distally of the buccal tube 15 and may or may not be welded or attached to the band 12 thereon. The device 10 is capable of sliding along the arch wire 16 in the direction of arrow C thereby acting as a "cinching" lock, allowing the arch wire 16 to move distally, however preventing the wire from mesial movement. It can be readily appreciated that such a configuration can allow for activation of spring mechanisms in the anterior or buccal segments of the arch wire.

Figure 10:
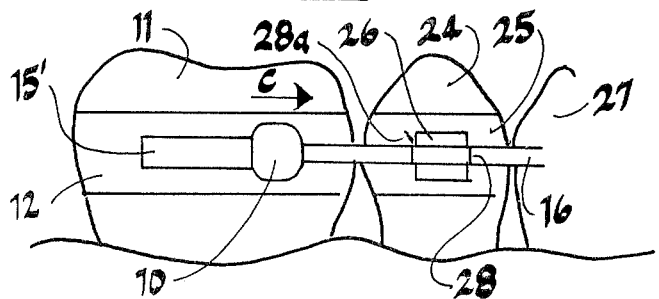
FIG. 10 is an elevation view including a device according to the invention mounted on a tooth by means of an orthodontic band and receiving an arch wire.

The arrangement of FIG. 10 is functionally similar to the arrangement of FIG. 9. In FIG. 10, the device 10 has been integrated with the buccal tube 15', the device 10 merely being welded to or integrally formed with the buccal tube 15' at the mesial end thereof, taking the place of the mesial end of the buccal tube 15 of the arrangement of FIG. 9. The device 10 functions in exactly the same way in the arrangement of FIG. 10 as it does in the arrangement of FIG. 9.

Figures 11, 12:
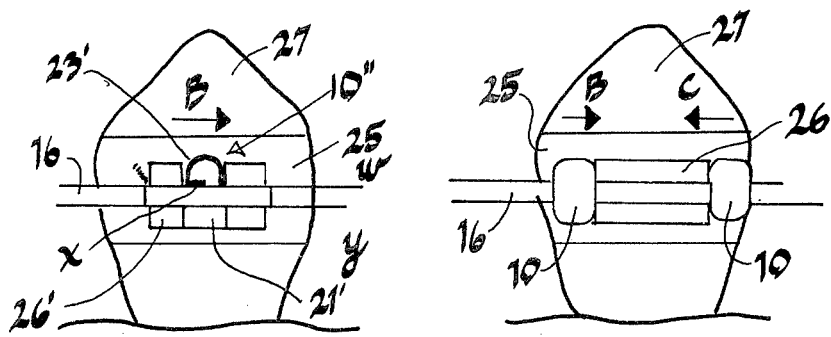
FIG. 11 is an elevation view including a device according to the invention in cross section integrated with a bracket on an orthodontic band mounted on a tooth, the device receiving an arch wire.
FIG. 12 is an elevation view including two devices according to the invention mounted on an arch wire.

In FIG. 11, the tooth 27 has a modified orthodontic bracket 26' mounted thereon. The bracket 26' is modified in that a device 10" according to the invention is integrated with it. The device 10" is, in principle, like the devices 10 and 10', being different only in structural detail. The device 10" includes a tension spring 23' having a free end x bearing downwardly against the upper surface of the arch wire 16 and another end integrally formed with or welded to a block-shaped anvil 21' on which the lower surface of the wire 16 rests. As illustrated, the device 10" would allow movement of the tooth along the wire 16 in the direction B. Inversion of the device 10" would, of course, allow the tooth to move along the wire in the direction opposite arrow B. The device as shown in FIG. 11 allows functional force movement.

FIG. 12 illustrates alternative embodiments in which the device 10 is mounted on the arch wire 16 both mesially and distally of the bracket 26, unattached in any way to the band 25. It is apparent that both devices 10 are oriented to have the facility of sliding along the arch wire in the respective directions of both arrows B and C, thereby locking the tooth 27 in its position relative to the wire and preventing the tooth from moving in either the mesial or distal directions along the wire. (It will, of course, be fully understood that in this and other applications of the devices of the invention, devices 10, 10' and 10" are interchangeable.)

Figure 13:
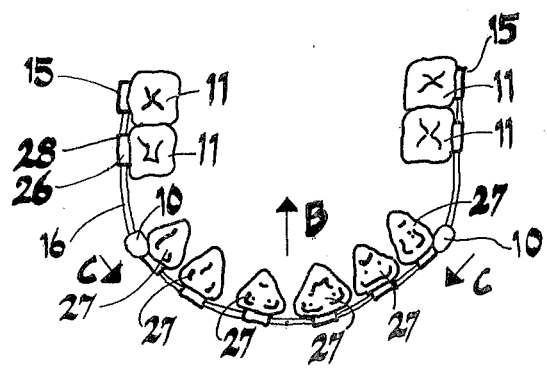
FIG. 13 is a plan view including a set of teeth, each tooth having mounted thereon an orthodontic band and a respective device according to the invention being mounted on the arch wire.
Figure 14:
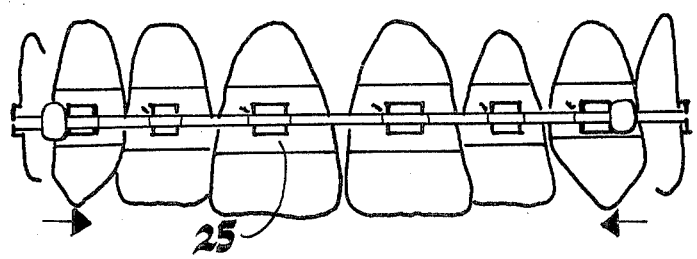
FIG. 14 is an elevation view corresponding to FIG. 13.

FIGS. 13 and 14 illustrate application of a pair of devices 10 of the invention to effect segment locking. The devices 10 are mounted on the wire only and are unattached to the orthodontic band surrounding the teeth 25. Thus the devices 10 are capable of movement in the directions of arrows C, thereby mechanically locking the anterior segment of the teeth together as a unit or urging them together to close up the minor illustrated gaps. The illustrated configuration makes the conventional prior art of "figure eighting" or the tying together of the individual teeth 27 of the aforementioned segments unnecessary. Further application of segment moving would involve additional devices 10 to be located at the buccal tubes 15 in the configurations as illustrated in FIGS. 9 and 10. These additional applications would allow, in conjunction with the applications illustrated in FIGS. 13 and 14 the entire lock segment of anterior teeth 27 to move distally (in the direction of arrow B in FIG. 13) to close the illustrated large gaps, using as anchors the molars 11. Both devices 10 are arranged to exert pressure mesially thereby to hold the teeth 27 together as that group of teeth is urged distally by the arch wire 16. The conventional arch wire 16, orthodontic bands 25, orthodontic brackets 26 and tie wires 28 are again being used.

Figure 15:
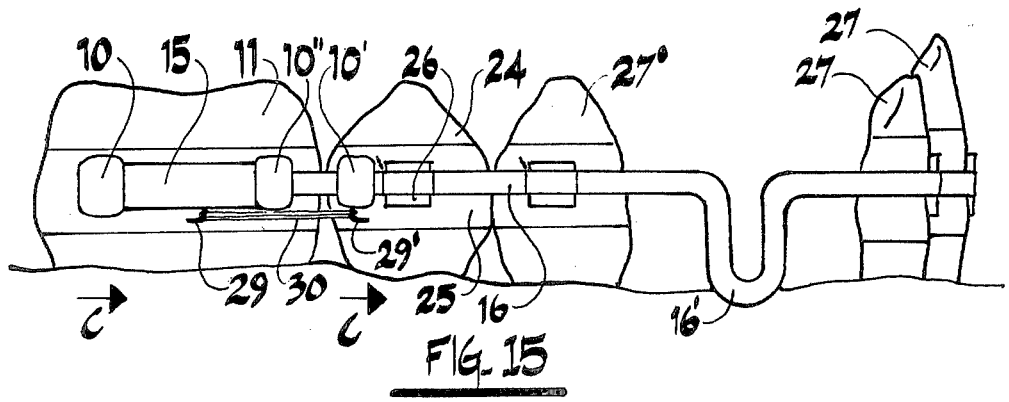
FIG. 15 is an elevation including teeth, orthodontic bands, devices according to the invention, an arch wire and an elastic.

In FIG. 15, the devices 10 are each individually used as a stop along the arch wire 16, allowing activation of the spring 16' to move individual teeth or segments of anterior teeth 27 distally. The bend 16' inserted in the arch wire 16 applies a tension to the wire 16 which, with the assistance of the device 10, tends to move the teeth 27 distally to close the illustrated gap. The arrangement of the device 10 of the invention relative to the buccal tube 15 on molar 11 is identical to FIG. 9, acting as a stop, activating the spring 16' and/or additional mechanics elsewhere along the arch wire 16. The arrangement of device 10" on molar 11 is identical to that illustrated in FIG. 10, acting as a stop activating the spring 16' and/or additional mechanics elsewhere along the arch wire 16. In an additional application for activation of spring 16' and/or additional mechanism elsewhere along the arch wire, a device 10' may be provided with a hook 29' and located as illustrated, capable of moving along the wire mesially (in the direction of arrow C) thereby locking itself on the wire whence a force is applied to it in the opposite direction. In addition, the buccal tube 15 will have a hook 29 welded thereto. An elastic 30 or wire tieback extends between the hooks 29 and 29'. In this instance, only the wire tieback 30 will activate the spring 16' and/or additional mechanics along the arch wire 16, resulting in distalization of teeth 27. Use of an elastic 30 extending between hooks 29 and 29' eliminates the need for the spring 16' but does however activate the arch wire as a unit resulting in distalization of teeth 27.

Figure 16:
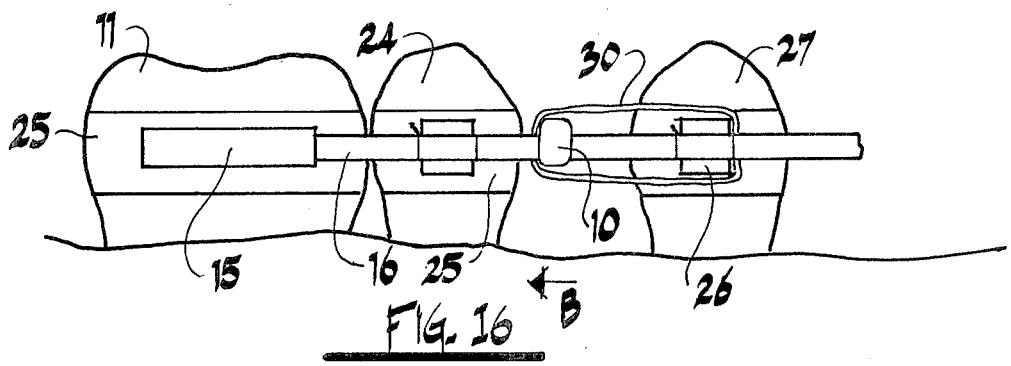
FIG. 16 is an elevation including teeth, orthodontic bands, a device according to the invention, an arch wire and an elastic.

In FIG. 16, a device 10 of the invention is mounted on a portion of the arch wire 16 bridging the gap between the premolar 24 and the other tooth 27. The device 10 is arranged to move distally (in the direction of arrow B), thereby locking itself upon the arch wire 16 whence a force is applied thereupon in the opposite direction of arrow B. An elastic 30 connects the device 10 to the bracket 26 on the tooth 27. Consequently, when this configuration is used with a molar stop as illustrated in FIG. 8 on the opposite side of either the mandibular or maxially arch, all teeth mesial to tooth 27 will serve as anchors to move tooth 27 distally. When the configuration of FIG. 16 is used with the "cinching" lock as illustrated in FIGS. 9 and 10, all teeth distal to tooth 27 becomes anchors in effect to move tooth 27 distally. In addition, the configuration of FIG. 16 may be used with "cinching" locks as illustrated in FIGS. 9 and 10 on the right and left molars 11, effecting bilateral mechanics as illustrated.

Adjustment of the above described locking devices of the invention is particularly easy considering that the tension springs may readily be temporarily pulled out of engagement with the arch wire by means of a conventional dental tooth such as a probe. Also, it can readily be appreciated that the locking device may be made in a hinged configuration so that it may be clamped onto the arch wire at any point along the length of the arch wire without threading the device onto the arch wire as in the illustrated embodiments. If a device according to the invention is used in such a way that the arch wire does not extend through the distal end of the device's passage, a plug may be inserted in that end to prevent the entry of debris or materials, such as cements, with which the orthodontist may be working. Moreover, plugs may be placed in both ends of the device to prevent cement or debris from entering the mechanism during placement of the device before insertion of the arch wire. Other modifications and variations will be obvious to those skilled in the art from considering the foregoing and it is intended that all such modifications and variations be within the scope of the hereto appended claims.

What is claimed is:

1. An orthodontic locking device for use with an arch wire having uniform surfaces, said device comprising means defining a passage for the insertion of the arch wire and means defining a tension spring for bearing against the arch wire the tension spring being oriented relative to the arch wire at an angle of less than 90°, the tension spring having a free end portion for bearing against the arch wire and being fixed at its other end, the free end portion of the tension spring always being in engagement with the arch wire so that movement of the arch wire toward said free end portion causes said free end portion to hield and movement of said arch wire away from said free end portion causes the free end portion to lock the arch wire.

2. An orthodontic device according to claim 1, further comprising a member having a channel defined through it, the channel being of larger cross section than the cross section of the arch wire thereby to permit free movement of the arch wire in the channel and the member being of smaller cross section than the passage in the device thereby to permit insertion of the member into the device, the spring bearing against the member instead of against the arch wire when the member is inserted in the device.

3. An orthodontic device according to claim 1 in combination with a buccal tube, the device being located mesially of the buccal tube.

4. An orthodontic device according to claim 1 in combination with a buccal tube, the device being located distally of the buccal tube.

5. An orthodontic device according to claim 1 in combination with a buccal tube, the device being integrated with the buccal tube.

6. An orthodontic device according to claim 1 in combination with an orthodontic bracket, the device being located mesially of the bracket.

7. An orthodontic device according to claim 1 in combination with an orthodontic bracket, the device being located distally of the bracket.

8. An orthodontic device according to claim 1 in combination with an orthodontic bracket, the device being integrated with the bracket.

* * * * *

UNITED STATES PATENT AND TRADEMARK OFFICE
CERTIFICATE OF CORRECTION

PATENT NO. : 4,192,070
DATED : March 11, 1980
INVENTOR(S) : Marc S. Lemchen et al It is certified that error appears in the above-identified patent and that said Letters Patent are hereby corrected as shown below:

Claim 1, line 12, change "hield" to --yield--.

Signed and Sealed this

Tenth Day of June 1980

[SEAL]

Attest:

SIDNEY A. DIAMOND

Attesting Officer

Commissioner of Patents and Trademarks